(12) United States Patent
Kelley

(10) Patent No.: US 8,894,699 B2
(45) Date of Patent: Nov. 25, 2014

(54) METHODS AND APPARATUS FOR SURGICAL ANASTOMOSIS

(75) Inventor: Jill Kelley, Tampa, FL (US)

(73) Assignee: Dr. Kelley Cancer Foundation, Tampa, FL (US)

( * ) Notice: Subject to any disclaimer, the term of this patent is extended or adjusted under 35 U.S.C. 154(b) by 622 days.

(21) Appl. No.: 12/099,067

(22) Filed: Apr. 7, 2008

(65) Prior Publication Data

US 2008/0255650 A1    Oct. 16, 2008

Related U.S. Application Data

(60) Provisional application No. 60/910,570, filed on Apr. 6, 2007.

(51) Int. Cl.
| | | |
|---|---|---|
| *A61F 2/06* | (2013.01) |
| *A61B 17/11* | (2006.01) |
| *A61F 2/04* | (2013.01) |
| *A61B 17/00* | (2006.01) |
| *A61B 17/08* | (2006.01) |

(52) U.S. Cl.
CPC ............. *A61B 17/11* (2013.01); *A61B 17/1114* (2013.01); *A61F 2/04* (2013.01); *A61F 2/064* (2013.01); *A61B 17/00491* (2013.01); *A61B 17/08* (2013.01)
USPC ....... 623/1.13; 623/1.11; 623/1.46; 623/1.15; 606/153; 606/154; 606/155

(58) Field of Classification Search
USPC ...................... 623/1.13, 1.2, 1.15, 1.42, 1.46, 623/23.64–23.71, 1.11, 1.35; 606/153, 154, 606/214, 8, 155
See application file for complete search history.

(56) References Cited

U.S. PATENT DOCUMENTS

| | | | | | |
|---|---|---|---|---|---|
| 1,470,707 | A | * | 10/1923 | Bates ............................ | 606/154 |
| 3,254,651 | A | * | 6/1966 | Collito .......................... | 606/153 |
| 5,064,057 | A | * | 11/1991 | Iwatsuki et al. ............... | 606/154 |
| 5,180,392 | A | * | 1/1993 | Skeie et al. ................. | 623/23.64 |
| 5,921,995 | A | * | 7/1999 | Kleshinski .................... | 606/153 |
| 2004/0186489 | A1 | * | 9/2004 | Lee ................................ | 606/153 |
| 2004/0254595 | A1 | * | 12/2004 | Richard et al. ................ | 606/153 |
| 2006/0271104 | A1 | * | 11/2006 | Viola et al. .................... | 606/214 |

OTHER PUBLICATIONS

International Search Report dated Sep. 4, 2008 for PCT/US2008/059489.

* cited by examiner

*Primary Examiner* — Tuan V Nguyen
*Assistant Examiner* — Tin Nguyen
(74) *Attorney, Agent, or Firm* — Larson & Larson, P.A.; Frank Liebenow; Justin P. Miller

(57) ABSTRACT

Methods and apparatus for anastomosis of a lumen according to various aspects of the present invention operate in conjunction with an impermeable stent. The impermeable stent may comprise a scaffold and, if needed, a sealant, such as a membrane and/or adhesive. In one embodiment, the scaffold, membrane and/or adhesive comprise biocompatible materials suitable for bio-absorption and/or degradation.

20 Claims, 5 Drawing Sheets

METHODS AND APPARATUS FOR SURGICAL ANASTOMOSIS

CROSS-REFERENCES TO RELATED APPLICATIONS

Figure 1:
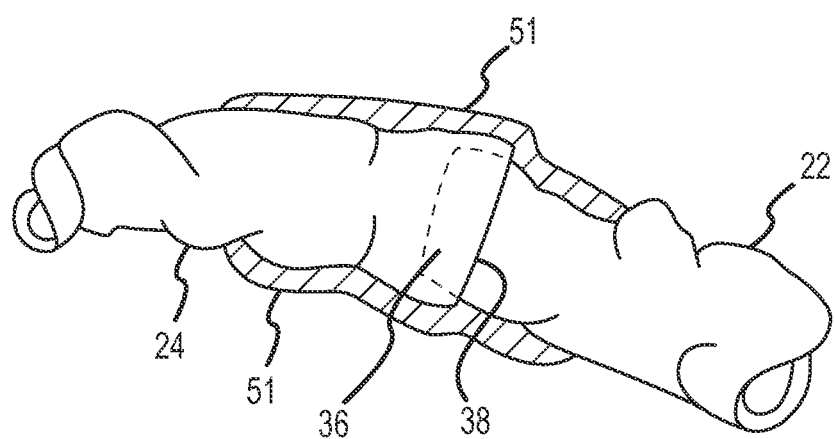

The present application claims the benefit of U.S. Provisional Patent Application Ser. No. 60/910,570, filed Apr. 6, 2007, entitled Scaffold and Method for Surgical Resection, and incorporates the disclosure of such application by reference.

BACKGROUND OF THE INVENTION

The gastrointestinal (GI) tract extends from the esophagus to the anus and senses many functions, including nutrition, hydration, and disease prevention. Resection of a portion of the GI tract, such as esophagus, small intestine, large intestine or colon, is performed on a patient under general anesthesia. An incision is typically made in the abdomen, chest or neck and a diseased portion is removed. The healthy ends that remain are sewn or stapled together and the incision is closed through the procedure known as anastomosis. There is substantial risk of the patient leaking at the site of the anastomosis even if the surgeon follows best practices. Leakage may lead to contamination of the peritoneal or thoracic cavity, sepsis and even death. Leakage may be evident immediately or it may be delayed at the site of anastomosis, regardless of the skill of the surgeon.

Although research to decrease failure rates of reseclion/anastomosis has been considerable, success has been elusive. Advances in minimally invasive procedures allow surgeons to perform resection and anastamoses using laparoscopic or thoracoscopic technologies. However, many surgeons are unwilling to use less invasive procedures due to the inherent risks of leakage and severity of the complications of leakage from the GI tract. As an alternative to connecting the two intestinal ends, the surgeon may perform an ostomy or stoma, exteriorizing a portion of the intestine and leaving a patient with an opening on the abdomen or neck. Such procedures, however, involve having the patient wear an external pouch to collect intestinal waste. Possible infection and restrictions on patient lifestyles make this option unattractive. If an anastomosed site leaks, then a surgeon often opts to perform an ostomy as a necessity to prevent any further sepsis, morbidity or death of the patient.

SUMMARY OF THE INVENTION

Methods and apparatus for anastomosis of a lumen according to various aspects of the present invention operate in conjunction with an impermeable stent. The impermeable stent may comprise a scaffold and, if needed, a sealant such as a membrane and/or adhesive. In one embodiment, the scaffold, membrane and/or adhesive comprise biocompatible materials suitable for bio-absorption and/or degradation.

BRIEF DESCRIPTION OF THE DRAWING FIGURES

A more complete understanding of the present invention may be derived by referring to the detailed description when considered in connection with the following illustrative figures. In the following figures, like reference numbers refer to similar elements and steps.

Figure 2:
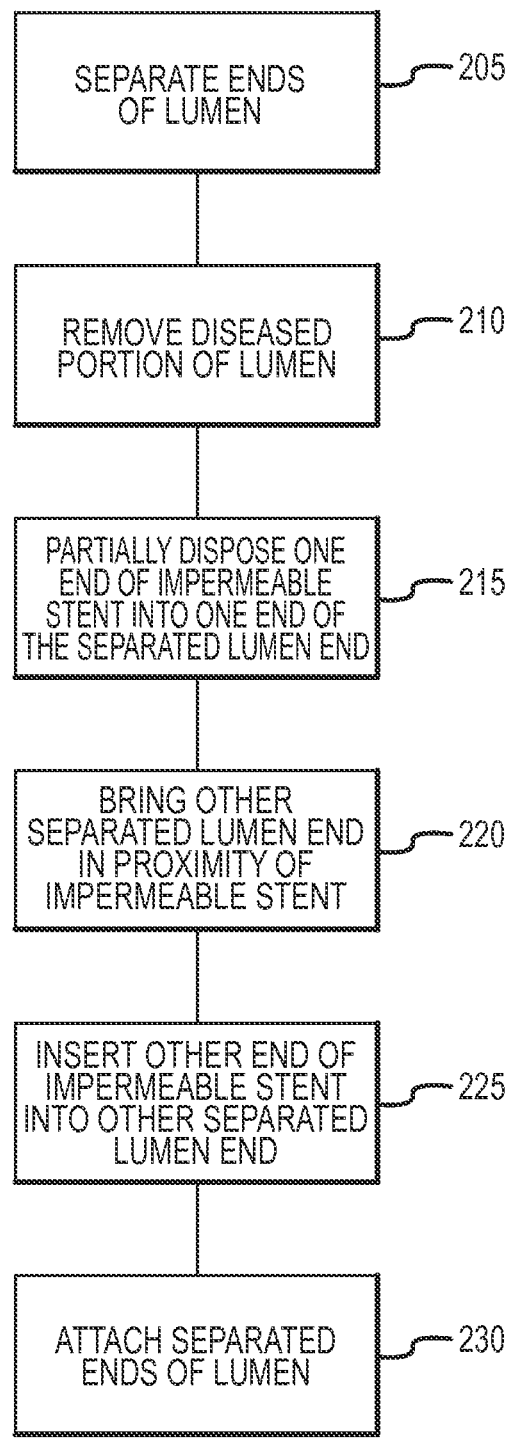
Figure 3:
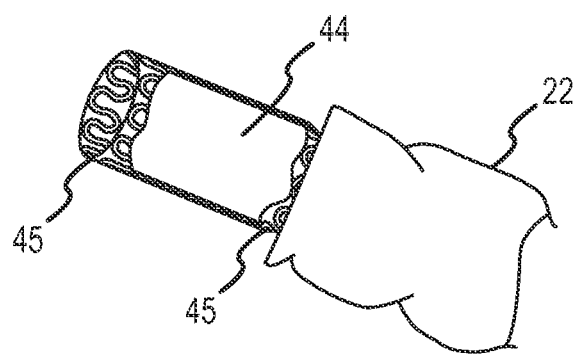
Figure 4:
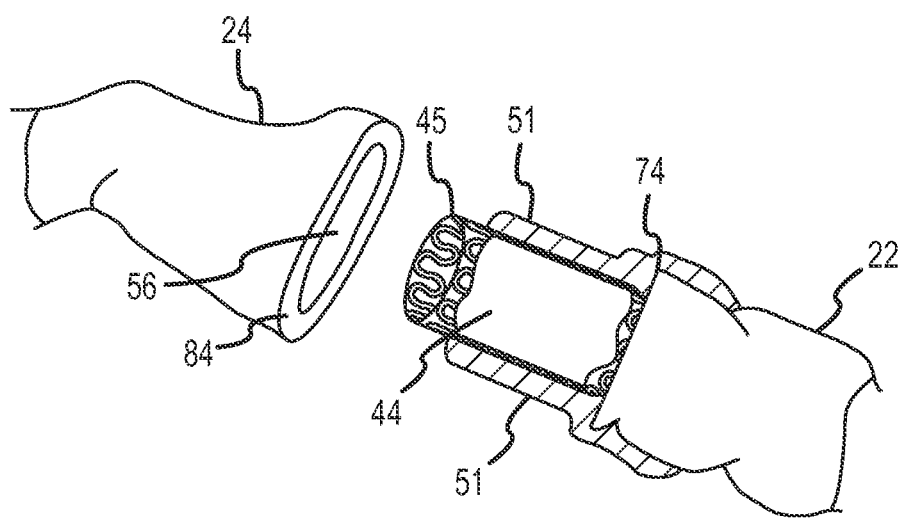
Figure 5:
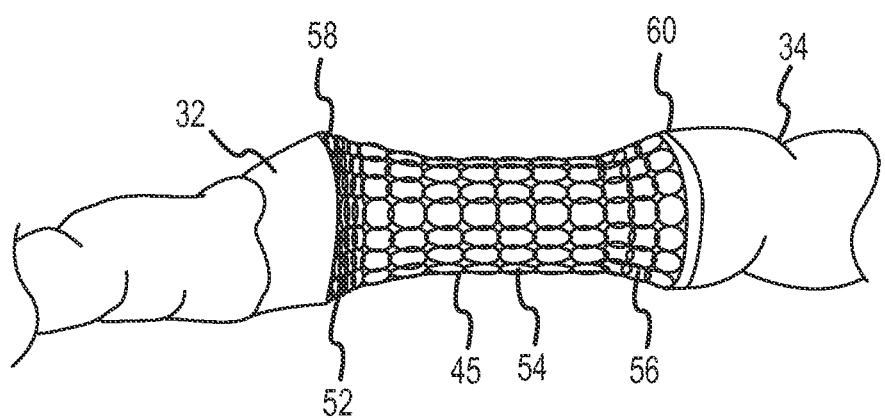

FIG. 1 illustrates an anastomosed intestinal lumen;
FIG. 2 is a flow chart of a method of anastomosis utilizing an impermeable stent;
FIG. 3 illustrates a scaffold inserted into a lumen end;
FIG. 4 illustrates an example of a second lumen end being placed over a scaffold covered by a membrane and prepared with an adhesive; and
FIG. 5 illustrates an example of a scaffold joining two lumen ends.

Elements and steps in the figures are illustrated for simplicity and clarity and have not necessarily been rendered according to any particular sequence. For example, steps that may be performed concurrently or in different order are illustrated in the figures to help to improve understanding of embodiments of the present invention.

DETAILED DESCRIPTION OF EXEMPLARY EMBODIMENTS

The present invention may be described in terms of functional block components and various processing steps. Such functional blocks may be realized by any number of elements configured to perform the specified functions and achieve the various results. For example, the present invention may be adapted for various stents, scaffolds, membranes, adhesives and the like. Thus, the present invention may employ various methods of resection, anastomosis and the like. The stents described are merely exemplary applications for the invention.

Methods and apparatus for anastomosis of a lumen according to various aspects of the present invention operate in conjunction with an impermeable stent. The impermeable stent may comprise a scaffold and, if needed, a sealant, such as a membrane and/or adhesive. The scaffold and sealant may be implemented in anastomosis of a lumen during another surgical procedure, such as, after resection of the lumen.

Briefly, referring to FIG. 2, a lumen, such as a colon or intestine, is separated [205] and a diseased portion is removed [210]. After removal, the surgeon may insert an impermeable stent, comprising the scaffold and a sealant, into one end of the separated lumen [215]. The second lumen end may be placed proximate the impermeable stent [220] and disposed over the impermeable stent [225]. The two lumen ends may be attached to each other or the impermeable stent using any suitable attachment procedure, such as suturing, stapling and/or use of an adhesive [230].

Methods and apparatus for anastomosis of a lumen according to various aspects of the present invention ma, provide various advantages to known methods of anastomosis. For example, use of an impermeable stent inserted during anastomosis to act as a prophylactic measure against leakage and/or soilage prevents the inconvenience and frequent complications associated with treating leaking anastomosed lumens. Additionally, the use of the scaffold may prevent scarring and may eliminate or reduce constrictions (strictures) caused by closure of the lumen, such as by scarring or fusion. In other embodiments, use of an impermeable stent may promote healing in the affected area of the lumen.

The impermeable stent according to various aspects of the present invention may provide an impermeable layer that inhibits leakage of anastomosed lumen ends. Referring now to FIGS. 1 and 3-5, in various embodiments, the impermeable stent comprises a scaffold 45 that may be inserted between and/or within the luminal ends 36, 38 of the anastomosed lumen 22, 24 to provide stability and/or structure to the anastomosed lumen 22, 24 and/or to function as an impermeable stent. In one embodiment, a membrane 44 may at least partially cover the scaffold 45 to provide an impermeable barrier and a prophylactic to inhibit leakage of the anastomosed lumen 22, 24. In another embodiment, an adhesive 51 may be applied to the external surface of the lumen 22, 24 and/or overlapping luminal ends 36, 38 to inhibit leakage of the anastomosed lumen.

Apparatus and methods of anastomosis may be applied to any lumen in a body, including lumen located in the gastrointestinal tract, the urinary tract, the cardiovascular system, the biliary tract, and the genitourinary tract. Suitable anastomosis sites may include the intestines, esophagus, stomach, bile ducts, pancreas, and urethra. In one embodiment, resection of the esophagus, colon or intestine may be performed to remove troublesome portions of luminal tissue, such as cancerous tissue. After resection, the separated lumen ends may be anastomosed, incorporating the impermeable stent comprising the scaffold 45 and if needed, the membrane 44, such as a sealant, to inhibit leakage.

The scaffold 45 may comprise any structure suitable for at least partial disposal within a luminal body. Additionally, the scaffold 45 may comprise any appropriate size, shape, texture and/or material. For example, the scaffold 45 may comprise a metal, plastic, nylon, or suitable synthetic and/or natural polymer. The scaffold 45 may be configured to comprise any symmetrical and/or asymmetrical geometric shape, including funnel-shapes and/or tubular shapes. Additionally, the scaffold 45 may be configured for custom sizing and/or shaping to conform to the contours of the lumen. In one embodiment, the scaffold 45 may comprise an internal framework for a joined lumen.

In one embodiment, the scaffold 45 may comprise a stent. For example, the scaffold 45 may comprise a conventional metal stent formed from a plurality of unit cells and may be configured to be pressure-expandable. The stent may be woven or chain-linked and may be configured for radial expansion through application of pressure and/or lateral force. In another embodiment, the scaffold may comprise a self-expanding stent. In yet another embodiment, the scaffold 45 may comprise an elastic, flexible stent including a thin-walled cylinder having woven elements. The flexible nature of the stent may provide a suitable scaffold 45 in applications where the scaffold 45 is not subsequently removed from the anastomosed lumen.

Referring now to FIG. 5, in one embodiment, the scaffold 45 may serve as an artificial lumen layer, such as an artificial intestinal layer or an artificial colon layer. To accommodate the shape and contours of the lumen, the scaffold 45 may comprise two differently shaped ends 58, 60 which are configured to connect to the ends of the lumen, such as for example, intestinal ends 32, 34.

The scaffold 45 may further comprise expandable loops 52, 54, 56. The expandable loops may comprise any suitable material, including polymers, such as nylon, and metals, such as titanium. To provide flexibility and/or malleability to the scaffold 45, the expandable loops 52, 54, 56 may be configured to expand axially and/or radially to substantially conform to the diameter of the lumen and/or the distance between the lumen ends 32, 34.

The scaffold 45 may also comprise a shape change material that is capable of undergoing a phase transition at a defined phase transition temperature. Suitable phase transition materials may include alloys of nickel and/or titanium. The shape change material may be configured to exhibit a phase change temperature that is less than the temperature of the luminal tissue surrounding the scaffold 45. Once inserted, the scaffold 45 warms, expanding and/or substantially conforming to the contours of the surrounding luminal tissue.

Further, the scaffold 45 may be placed in conjunction with a balloon. For example, a balloon mechanism may be inserted inside a partially collapsed scaffold 45, and the balloon scaffold 45 combination may be inserted into place between and/or at least partially within the separated lumen ends. Once in place, the balloon may be expanded to radially expand the scaffold 45. The expansion of the balloon may be performed in any appropriate manner, such as pneumatically and/or hydraulically.

The balloon may be further configured to expand the scaffold 45 so that the scaffold 45 makes contact with the surrounding luminal tissue for attachment and/or support. For example, where adhesive 51 is applied to at least part of the external surface of the scaffold 45 and/or at least part of the internal surface of the luminal tissue, the balloon may provide a mechanism for holding the scaffold 45 in place while the adhesive sets.

Once the scaffold 45 is in place and/or attached to the luminal tissue or membrane, the balloon may be disengaged and removed. Alternatively, the balloon and scaffold 45 combination may be removed together once lumen ends have been successfully joined.

The scaffold 45 may also comprise a biocompatible, biodegradable and/or bioabsorbable material. Once the scaffold 45 is in place, it may disintegrate over time, and either become absorbed into or pass through the body. Thus, the scaffold 45 may be removed without the necessity for mechanical removal, a more invasive procedure. For example, in an application where the scaffold 45 is internal to the anastomosed lumen and/or where an impermeable membrane is connected between the separated lumen ends, the scaffold 45 may no longer be necessary to provide structure and/or support to the lumen, and it may be desirable for the scaffold 45 to disintegrate or be absorbed by the body.

In various embodiments of the present invention, the scaffold 45 is implemented in conjunction with an impermeable layer, such as sealant, to function as an impermeable stent to prevent leakage at a site of anastomosis. The sealant may comprise any biocompatible impermeable layer suitable for covering the scaffold 45. In one embodiment, the sealant may include a membrane that is wrapped, rolled and/or otherwise placed around the scaffold 45. In another embodiment, the sealant may include a layer of adhesive 51.

The membrane may comprise any suitable material for placement in contact with luminal tissue and/or around the scaffold 45. For example, the membrane may include biocompatible, biodegradable and/or bioabsorbable synthetic and/or natural materials. Additionally, the membrane may comprise any suitable size, shape texture and/or number of layers. In one embodiment, the membrane is impermeable and may be implemented to provide a substantially leak-free seal when applied to joined luminal ends and/or on exposed portions of the scaffold 45.

Referring to FIG. 3, the membrane 44 may placed around the scaffold 45 to substantially cover it as the scaffold 45 is partially disposed within a lumen end 22. The membrane 44 may be placed on the scaffold 45 before, during or after insertion of the scaffold 45 at the anastomosed site. Additionally, the membrane 44 may comprise a substantially homogenous sheet and may be wrapped and/or rolled around the scaffold 45. In another embodiment, the membrane 44 may comprise multiple pieces that are placed in an abutting and/or overlapping position on the scaffold 45.

Referring to FIG. 4, the membrane 44 may abut and/or be at least partially disposed within the lumen 22, and may rest between the scaffold 45 and the internal tissue of the lumen 22. The membrane 44 may be secured by applying the adhesive 51 between the scaffold 45 and the membrane 44, between the membrane 44 and/or scaffold 45 and the internal luminal tissue at and/or near the lumen end 74, and/or around the membrane 44, luminal end 74, and/or part of the lumen 22. One or more fixation devices may also be implemented to secure the membrane 44 to the scaffold 45 and/or luminal tissue 74, such as a tack, spiral wire, staple and/or sutures.

In another embodiment, the scaffold 45 and/or membrane 44 may include a composition to promote healing, such as a growth factor, antimicrobial agent, antibody and/or the like. Growth factors comprise cellular proteins that assist in cellular proliferation and differentiation. Antimicrobial agents, including antivirals, antibiotics and antifungals, prevent harmful bacteria, viruses and/or other microbes from infecting the anastomosed site and interfering with the tissue healing and growth processes. Certain types of antibodies may be implemented to bind with foreign objects, such as bacteria and viruses that would be harmful to the healing site if not contained.

Adhesives according to various aspects of the present invention may comprise any suitable material to attach, adhere and/or bond to living tissue. Adhesives may comprise natural, naturally derived and/or synthetic materials. The adhesive 51 may comprise any suitable consistency, texture, weight, viscosity and/or level of transparency to be used to bond and/or seal lumen ends, the scaffold 45 and/or the membrane 44. The adhesive 51 may comprise a gel, liquid and/or solid.

In one embodiment, the adhesive 51 may comprise a biocompatible, biodegradable and/or bioabsorbable material. For example, in one embodiment, the adhesive may include purified bovine serum albumin and glutaraldehyde, sold commercially as Bioglue® by Cryolife Technology, Inc., Kennesaw Ga. In another embodiment, the adhesive may comprise polyethylene glycol, sold commercially as Duraseal® Sealant by Confluent Surgical, Inc., Waltham, Mass.

Suitable methods of application of the adhesive 51 may include spraying, topical application and/or injection. In one embodiment, a more viscous adhesive, such as Duraseal® Sealant may be applied to decrease the setting time. By decreasing the setting time of the adhesive 51, the time required for a surgeon to hold the ends of lumen 36, 38 together or the ends of a lumen against a scaffold 45 and/or membrane 44 is decreased.

The adhesive 51 may provide both a mechanism for attachment of lumen ends to each other (either directly or via a scaffold 45 and/or membrane 44) after anastomosis, as well as a sealant to inhibit leakage after reattachment. For example, as shown in FIG. 1, the adhesive 51 may be applied over joined and/or overlapping ends 36, 38 of the lumen 22, 24. In another embodiment, the adhesive 51 may bond the scaffold 45 to the lumen ends 36, 38 and may seal the connection between the scaffold 45 and lumen ends 36, 38 to inhibit leakage. In yet another embodiment, the adhesive 51 may be applied over the scaffold 45 and the lumen ends 36, 38 to both bond the lumen ends 36, 38 to the scaffold 45, as well as provide a seal to inhibit leakage.

In one embodiment, once a biocompatible, biodegradable and/or bioabsorbable adhesive 51 is in place it may be configured to disintegrate, degrade and either become absorbed into or pass through the body. For example, in an application where the lumen ends 36, 38 are configured to heal and reseal themselves, the adhesive 51 may no longer be necessary to bond and/or seal the lumen, and it may desirable for the adhesive 51 to be removed.

The particular implementations shown and described are illustrative of the invention and its best mode and are not intended to otherwise limit the scope of the present invention in any way. Indeed, for the sake of brevity, conventional resection and anastomosis methods, stents and scaffolds and methods for insertion, tissue healing and growing mechanisms, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

The present invention has been described above with reference to a particular embodiment. However, changes and modifications may be made to the particular embodiment without departing from the scope of the present invention. These and other changes or modifications are intended to be included within the scope of the present invention.

The invention claimed is:

1. A method for prophylactically treating leakage of a lumen during anastomosis of separated ends of the lumen by providing an impermeable stent, comprising:
   during a surgery, applying a sealant to an external surface of a scaffold;
   next, at least partially disposing the scaffold into separated ends of the lumen;
   attaching the scaffold to internal surfaces of the separated ends of the lumen via the sealant; and
   finally, attaching the separated ends of the lumen to one another after disposing the scaffold into the separated ends of the lumen such that the separated ends are in contact with one another.

2. The method of claim 1, wherein the sealant is an adhesive.

3. The method of claim 2, wherein the adhesive comprises at least one of: purified bovine serum albumin in combination with glutaraldehyde, and polyethylene glycol.

4. The method of claim 1, wherein the sealant comprises at least one of bioabsorbable material and biodegradable material.

5. The method of claim 1, wherein the scaffold comprises at least one of a bioabsorbable material and biodegradable material.

6. The method of claim 1, further comprising the step of providing at least one of a growth factor, an antimicrobial agent, and an antibody.

7. The method of claim 1, wherein the scaffold is at least one of expandable and removable.

8. The method of claim 1, wherein attaching the separated lumen ends to one another includes attaching the separated lumen ends via a fixation device including at least one of: an adhesive, a tack, a spiral wire, a staple, and a suture.

9. The method of claim 8, further comprising attaching the scaffold to at least one separated lumen end.

10. The method of claim 8, wherein the fixation device comprises at least one of a bioabsorbable material and biodegradable material.

11. The method of claim 1, further comprising the step of disposing a balloon within the scaffold, wherein the balloon is configured to radially expand the scaffold to contact the surface of the inner luminal tissue.

12. The method of claim 1, further comprising forming the scaffold from a shape change material.

13. The method of claim 12, further comprising radially expanding the scaffold following attachment of the scaffold to the internal surfaces of the separated ends of the lumen by warming the shape change material of the scaffold.

14. The method of claim 13, wherein warming the shape change material includes supplying heat to the shape change material from the lumen.

15. The method of claim 12, wherein forming the scaffold from a shape change material includes forming the scaffold from a shape change material that has a phase change temperature that is less than a temperature of the lumen.

16. A method for prophylactically treating leakage of a lumen during anastomosis of separated ends of the lumen by providing an impermeable stent, comprising:
   during a surgery, applying a sealant to an external surface of a scaffold and to an external surface of at least one of the separated ends of the lumen;
   next, at least partially disposing the scaffold into separated ends of the lumen;
   attaching the scaffold to internal surfaces of the separated ends of the lumen via the sealant; and
   finally, attaching the separated ends of the lumen to one another after disposing the scaffold into the separated ends of the lumen such that the separated ends are in contact with one another.

17. The method of claim 16, wherein the sealant is an adhesive.

18. The method of claim 17, wherein the adhesive comprises at least one of: purified bovine serum albumin in combination with glutaraldehyde, and polyethylene glycol.

19. The method of claim 16, wherein the sealant comprises at least one of bioabsorbable material and biodegradable material.

20. The method of claim 16, wherein the scaffold comprises at least one of a bioabsorbable material and biodegradable material.

* * * * *